United States Patent [19]

Milbocker

[11] Patent Number: 5,106,184
[45] Date of Patent: Apr. 21, 1992

[54] RETINAL LASER DOPPLER APPARATUS HAVING EYE TRACKING SYSTEM

[75] Inventor: Michael T. Milbocker, Somerville, Mass.

[73] Assignee: Eye Research Institute of Retina Foundation, Boston, Mass.

[21] Appl. No.: 566,668

[22] Filed: Aug. 13, 1990

[51] Int. Cl.[5] .............................................. A61B 3/10
[52] U.S. Cl. .................................. 351/221; 351/205; 351/210; 351/246; 128/745
[58] Field of Search ............... 351/205, 210, 221, 246; 128/745, 691, 633; 356/39; 606/4

[56] References Cited

U.S. PATENT DOCUMENTS

| | | | |
|---|---|---|---|
| 4,346,991 | 8/1982 | Gardner et al. | 351/221 X |
| 4,856,891 | 8/1989 | Pflibsen et al. | 351/210 |
| 4,895,159 | 1/1990 | Weiss . | |
| 5,025,785 | 6/1991 | Weiss . | |

OTHER PUBLICATIONS

Petrig et al., Retinal Laser Doppler Velocimetry: Towards Its Computer-Assisted Clinical Use, Applied Optics, vol. 27:6, Mar. 1988, pp. 1126-1134.
"Laser Doppler Technique for Absolute Measurement of Blood Speed in Retinal Vessels", Feke et al., IEEE Transactions on Biomedical Engineering, vol. BME-34, Sep. 1987.
"Blow Flow in the Normal Human Retina", Feke et al., Investigative Ophthalmology & Visual Science, vol. 30, No. 1, Jan. 1989, pp. 58-65.
"Retinal Hemodynamics in Middle-Aged Normal Subjects", Feke et al., ARVO, No. 1879-20, poster presentation, May 3, 1990, abstract of Annual Meeting, p. 382.
"A Stabilized Bidirectional Laser Doppler Velocimeter", Milbocker et al., ARVO, No. 2786, paper presentation, May 4, 1990, abstract of Annual Meeting, p. 568.

*Primary Examiner*—Rodney B. Bovernick
*Attorney, Agent, or Firm*—Lahive & Cockfield

[57] ABSTRACT

A retinal blood flow velocimeter projects an illumination beam through a steering system onto a retinal vessel, and forms a separate tracking image back through the steering system. A fast tracking loop detects motion of the tracking image and moves the steering system to null image motion and keep the illumination beam centered on the vessel. The beam is reflected from the vessel, picked up by detectors at two fixed angles, and processed by spectral analysis. In one preferred embodiment the illumination beam and the steering system follow entirely separate paths through the steering system. Fiber optics translate the collected Doppler light without dispersion while preserving phase relationships, and absolute dimensions are determined from the image tracking electronics. A processor then computes volumetric blood flow which it compares with normative data.

27 Claims, 7 Drawing Sheets

RETINAL LASER DOPPLER APPARATUS HAVING EYE TRACKING SYSTEM

BACKGROUND OF THE INVENTION

The present invention relates to instrumentation for measuring blood flow in vessels of the retina by Doppler velocimetry.

The general theory of laser Doppler velocimetry, as applied to the measurement of a flowing fluid such as blood inside a blood vessel, is a well known application of flow measurement technology. Briefly, monochromatic light aimed at the vessel and into the flowing blood is reflected by the blood cells as diffuse light with a frequency distribution corresponding to the components of velocity of the individual scatterers. By analyzing the frequency distribution of the reflected light at two fixed receivers with a known separation angle, the velocity or, ideally, the velocity profile of the flowing blood can be deduced.

When one attempts to apply this approach to detect blood flow rates in vessels of the retina, however, practical obstacles are encountered. First, individual retinal vessels have a diameter under several hundred microns, so that in order to perform a reliable measurement it is necessary to aim a beam of laser light of diameter approximately equal to the diameter of the vessel. Smaller beam diameters introduce the risk of missing the centerline flow measurement, while larger beam diameters result in a lower signal to background ratio.

Second, the Doppler analysis requires collection of the reflected light from two distinct directions having a specified angular separation. This light collection must be done outside the eye. The optical paths therefore will vary depending on the curvatures of the eye involved, and the collected light will include extraneous light due to reflection at various surfaces of the eye.

Third, it is necessary to perform this aiming and to collect a sufficiently strong return signal, despite relatively fast and large scale movements of the eyeball.

When it is considered that a small diameter beam must be used to maintain an acceptable signal to noise ratio, and that the level of reflected light from the fundus that can be collected outside the eye is highly attenuated, the foregoing obstacles are seen to impose severe limits on the quality of collected light available for Doppler analysis.

These difficulties have heretofore limited the clinical applicability of laser Doppler velocimetry to carefully controlled and rather cumbersome analytical investigations. Typically, the procedure is done by fitting a rectifying lens directly on the cornea, and then, with the illumination and collection optics manually positioned on a target vessel, recording short time segments of the collected spectra. A large number of such recordings are then analyzed and segments are pieced together to obtain an analytically derived synthetic recording representing the flow during one or more entire heartbeat intervals. The analysis and ultimate synthesis or identification of a representative one- or two-second Doppler spectrum is done some time after the recording, so that blood flow information is not quickly provided.

One approach to simplifying the processing of the recorded Doppler spectra is to develop algorithms for initially selecting only those recorded spectrum segments which meet certain criteria representative of the expected flow functions. Highly noisy or anomalous recording segments are discarded, thus limiting the amount of remaining data that must be processed. This approach, while clearly eliminating records resulting, for example, when the beam misses a vessel entirely, may screen out some valid flow information and render the system blind to clinically significant details. Analysis of Doppler records would be simplified if the instrumentation could be aimed with sufficient stability to record a continuous record having a duration of a full heartbeat interval or longer. More meaningful measurements of blood flow could also be obtained if the stability were sufficient to allow aiming a Doppler illumination spot on a central region of a blood vessel and on smaller vessels.

SUMMARY OF THE INVENTION

It is an object of the invention to provide a retinal Doppler velocimeter of enhanced utility and performance.

It is another object of the invention to provide a retinal Doppler velocimeter which is reliably positioned and maintained on a retinal vessel.

It is another object of the invention to provide a retinal Doppler velocimeter which provides continuous or real time vessel flow information.

These and other desirable features are achieved in accordance with one embodiment of the invention by providing an optical beam steering system for controllably steering a beam directed at the retina, and by projecting a Doppler illumination beam through the steering system in a forward direction while forming an image of the retina along an optical path that passes through the steering system in a reverse direction. A tracking system detects motion of the image and develops control signals to produce compensating motions of the steering system so that the Doppler illumination beam remains centered on a thin blood vessel. With the illumination thus stabilized, a set of collection optics collects the light reflected from a retinal vessel along two distinct directions and an analyzer determines the spectrum of collected light, and preferably also computes or displays at least one of the peak or minimum velocity, the time-averaged centerline velocity, or the corresponding volumetric flow rate.

The steering system contains optical elements arranged so that the forward and reverse optical paths are separated.

In a preferred embodiment, the Doppler collection optics are located behind the steering system to provide an unobstructed area between the instrument and the eye, and are positioned so the angles at which the light is collected bear a fixed angular offset.

The steering system includes a pair of two sided mirror elements, each pivotable about one of two mutually orthogonal steering axes, and an optical relay system which places a face of each mirror element in a conjugate relation to a face of the other mirror element.

In another or further preferred embodiment of the system, the blood vessel is imaged as a tracking target transversely onto a linear CCD array, which provides a direct measure of the vessel diameter. A processor computes the vessel's volumetric flow rate as a function of centerline blood flow velocity and vessel diameter. In a further embodiment according to this aspect of the invention, the processor may include a stored table of normal flow rates as a function of vessel size and the subject's age, and may provide a diagnostic output based on a comparison of the detected and the normal flow. In another embodiment, the processor may store diagnostic programs for summing the flow over several vessels and detecting discrepancies indicative of flow pathologies.

BRIEF DESCRIPTION OF THE DRAWINGS

These and other features will be understood by reference to the following description of illustrative embodiments of the invention, together with the drawings, wherein.

DETAILED DESCRIPTION

Figure 1:
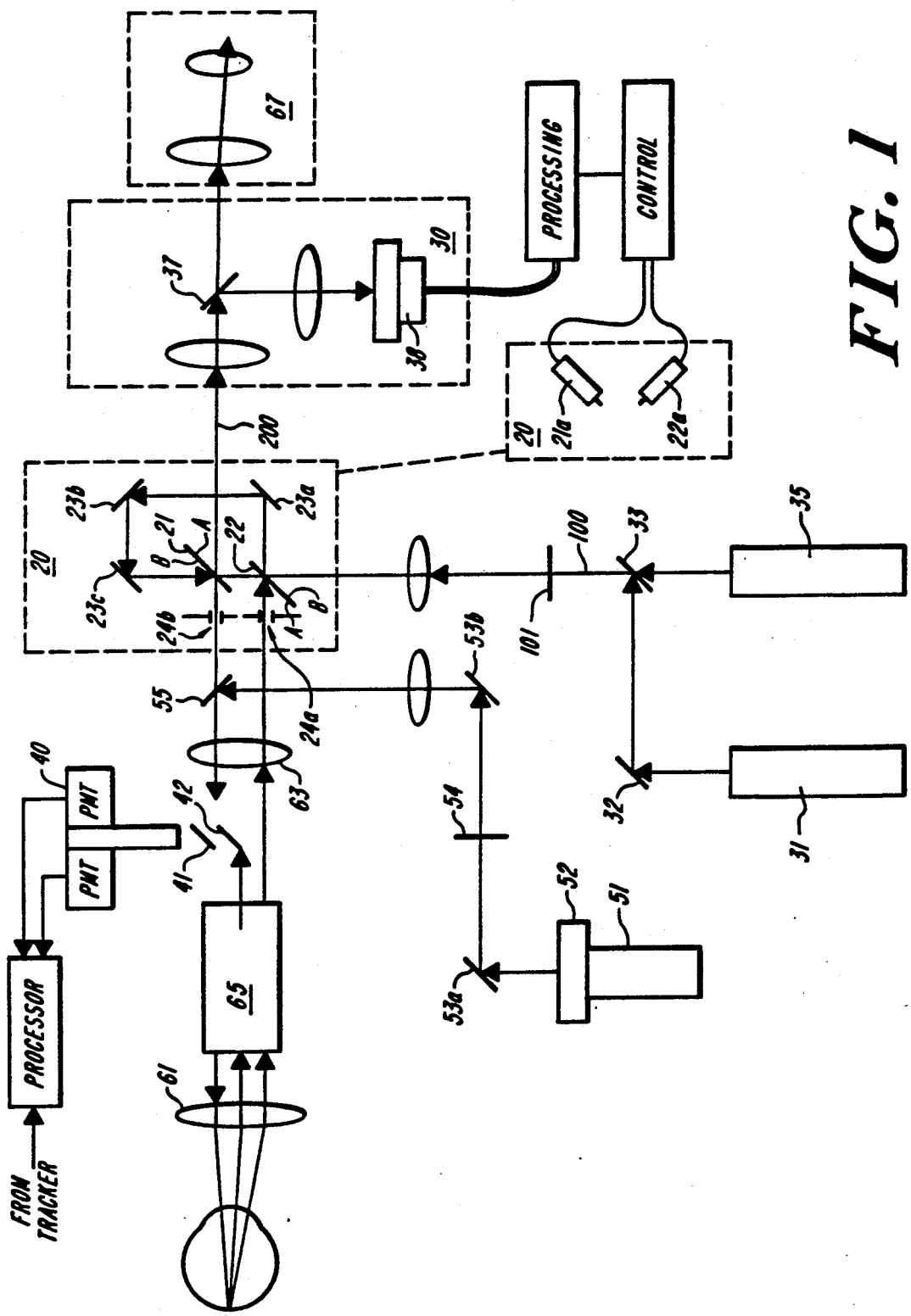
FIG. 1 illustrates one embodiment of the invention.

FIG. 1 illustrates a stabilized retinal laser Doppler system 10 in accordance with one embodiment of the present invention. System 10 includes a steering assembly 20, a tracking assembly 30, a red laser source 35 for illuminating a retinal vessel, and a two-channel Doppler pick up and analysis assembly 40. The steering assembly, which includes x- and y- axis deflection mirrors, is controlled by electrical signals to direct the optical path 100 of the beam from the red laser to a desired retinal vessel, and the beam is maintained centered on the targeted vessel by a tracking system which monitors the position of the image of the same or a nearby retinal blood vessel which has been imaged back through the same steering system into an electronic sensor array, e.g., a CCD 38. Change in position of the image on the CCD array is detected and used to develop control signals that reposition the steering mirrors to prevent motion of the image. The techniques for deriving a well defined tracking signal and controlling the mirrors with a sufficient speed and accuracy to aim the beam from laser 35 on a retinal target are described in U.S. Pat. No. 4,856,891 commonly owned by the assignee of the present invention, and the text of that patent is hereby incorporated herein by reference for purposes of a complete description and full disclosure.

The red laser light scattered from a targeted retinal vessel at the back of the eye is imaged by the eye objective optics back toward the steering system and is deflected by a pair of mirrors 41, 42 each having a diameter of approximately one millimeter and spaced approximately six millimeters apart. These mirrors reflect collected light into respective channels of the Doppler analysis unit. The mirrors each intercept about 1.4° of arc, and their spacing, corrected for the 3× magnification of the objective assembly, corresponds to a fixed divergence angle within the eye which allows calculation of absolute flow velocity values, when given the axial length of the subject's eye.

Observation light for the system is provided by a yellow helium-neon laser 51, which is directed through a beam expander 52, past deflecting mirrors 53a, 53b, and through an attenuator 54 to provide a broad field beam which is folded into the illumination path by beamsplitting mirror 55. The beam illuminates a ±10° field of the fundus.

Yellow observation light reflected from the fundus is returned through the objective assembly consisting of lenses 61, 63 and an image rotator 65, and passes through the steering assembly to an eyepiece or viewing assembly 67 where it provides a visible image field that moves synchronously with the tracking image and with the targeted vessel and Doppler illumination spot. The viewing assembly may include a camera. The function of the image rotator 65, described more fully in the aforesaid U.S. Patent, is simply to rotate a tracking image, such as the image of a retinal vessel, into a fixed orthogonal frame on the CCD. This allows the tracker to lock onto an obliquely oriented vessel and apply its fixed-frame orthogonal steering corrections. The image rotator thus provides additional convenience in setting up the instrument, and removes the need for image field transform computations in the tracking system.

In this illustrated embodiment, a green helium-neon laser 31 is provided for the tracking system. Laser 31 provides a separate beam which is folded into the same optical path 100 as that followed by the Doppler illumination beam by a turning mirror 32 and a beam splitting mirror 33, so that the green beam is also steered by the steering assembly 20. An attenuator 101 in the path limits the intensity of the steered beam. The green tracking beam has a small diameter, e.g., under several millimeters, and thus beneficially limits the illuminated area of the eye. The wavelength separation of the three described light sources allows appropriately placed filters or dichroic beam splitters to eliminate interference from each of the different sources on the viewing or sensing units associated with the other sources. For example, the beamsplitter 37 which reflects the return tracking image to the CCD 38 may be a dichroic beamsplitter which reflects substantially all the green light toward the CCD, while passing substantially all the yellow light to the observation optics 67. Further concrete examples of appropriate spectral separation paths are more fully described in the aforesaid U.S. patent.

The steering system 20 includes two steering mirrors 21, 22 each arranged to pivot about one of two orthogonal axes lying in a common plane P which is conjugate to the eye fundus. A galvanometer control 21a, 22a attached to a pivot shaft moves each mirror so that it is precisely turned to a direction within an angular range of approximately ±1020 . Each mirror has first and second sides, denoted the A (or inside) and the B (or outside faces) herein, and according to a Principal aspect to the invention these mirrors are arranged to maintain optical separation of the input and output light paths.

This separation is achieved by an optical relay system which translates the outside faces of the mirrors to each other, preferably including lenses or focusing mirrors which place the turning axis of the one mirror conjugate a plane containing to the turning axis of the other mirror with a 1:1 magnification. Such conjugation optics are more fully described in the co-pending United States Patent application Ser. No. 522,376 of Yakov Reznichenko and Michael Milbocker entitled Bidirectional Light Steering Apparatus, filed on May 11, 1990 and commonly owned by the assignee of the present invention. Said patent application is hereby incorporated herein by reference.

For ease of illustration, however, the intermediate lenses or curved reflective surfaces are omitted from the drawing, and the optical relay system is shown simply by three flat mirrors 23a, 23b, 23c which translate a beam impinging on the B face of one steering mirror to the B face of the other steering mirror. As further described in the aforesaid patent application, the steering mirrors may be thin plates which are metallized on one side, but are preferably front-surface mirrors metallized on both sides. This construction more effectively eliminates ghosting and internal reflection from the steering system.

The return image along axis RI from the subject's eye is reflected from the "A" face of mirror 22 to the "A" face of mirror 21, and thus passes through the steering system with the same angular deflection as a reverse-steered beam 200 passing to the tracking and observation optics, so that the light input beam 100 and the return image beam 200 always follow substantially fixed directions to and from the tracking/observation optics. A pair of diaphragms 24a, 24b located in a fundus conjugate plane screen out corneal and other reflections. The diaphragm opening is approximately ten millimeters.

Figure 3:
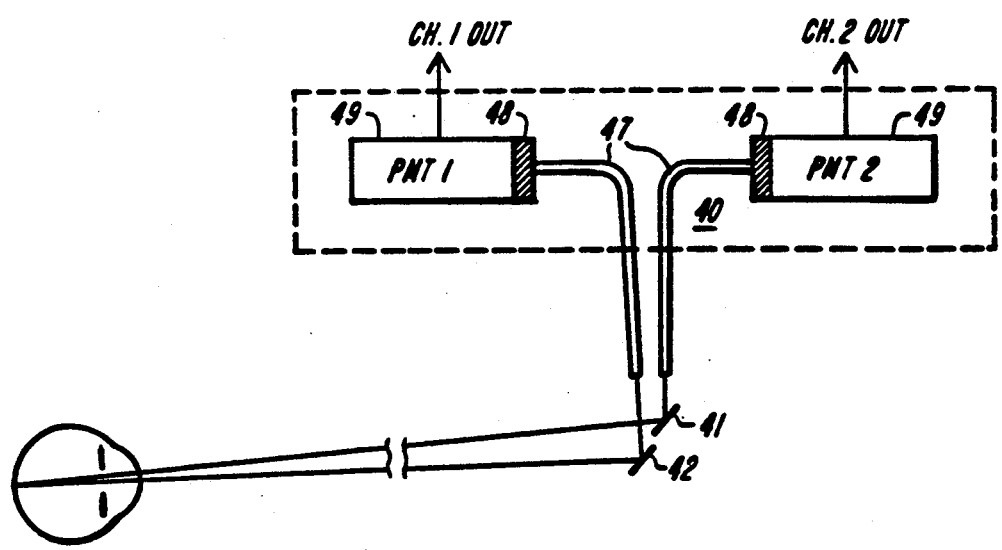
FIG. 3 illustrates the Doppler collection optics of the apparatus of FIG. 1 or 2.

Turning briefly to FIG. 3, the Doppler signal reception assembly 40 of FIG. 1 is illustrated in greater detail. The pick-off mirrors 41, 42 deflect two portions of the reflected Doppler beam which define in this embodiment a precise angular separation corresponding to a 13.5° divergence outside the eye. The light is relayed to a fiber bundle 47 in each channel. Each bundle 47 serves to channel the light received at one end of the bundle without further divergence or attenuation, while preserving phase relationships, to a photomultiplier tube 49 (RCA 8645). A red laser line filter 48 (Melles Griot 632.8 nm) removes extraneous wavelengths.

Figure 3A:
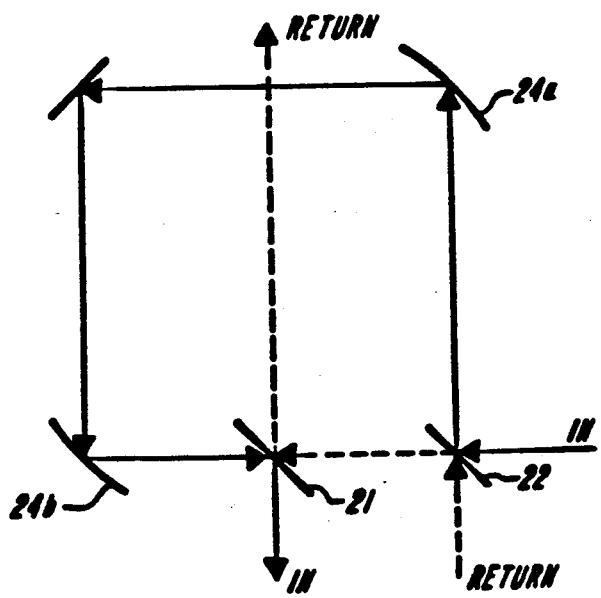
FIG. 3A illustrates alternate optics of the steering assembly.
Figure 3B:
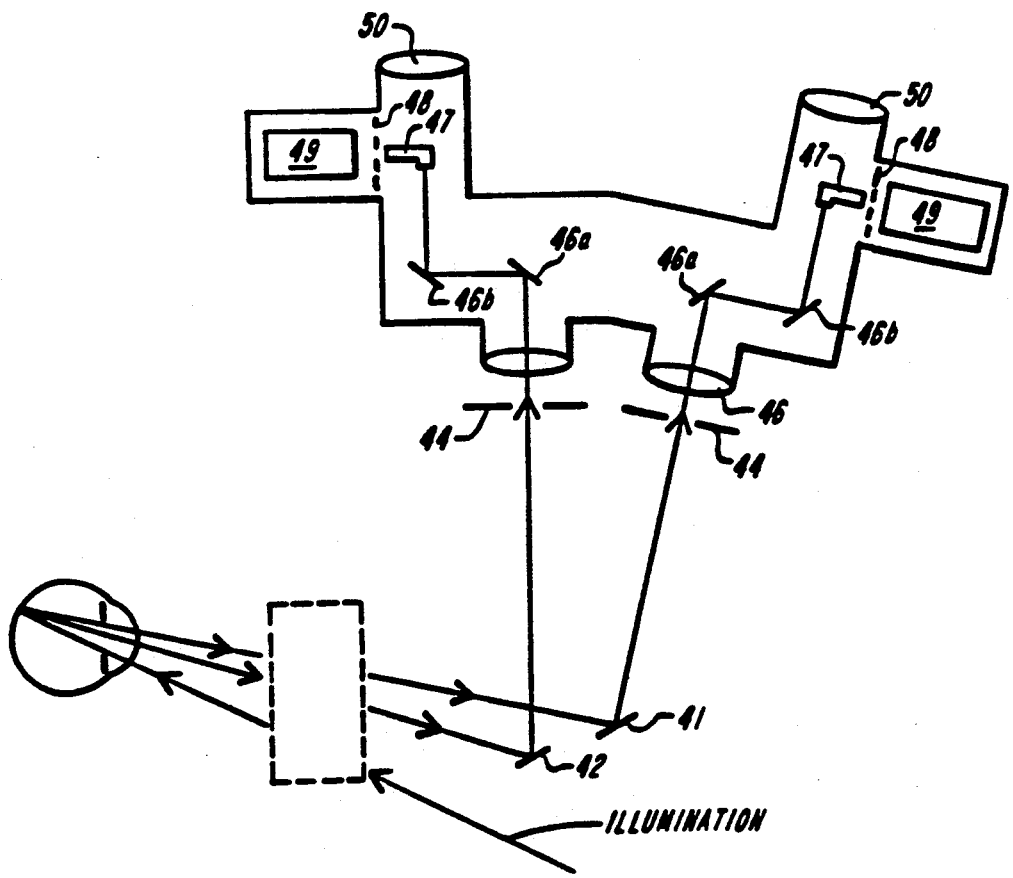
FIG. 3B illustrates alternate optics of the Doppler collection apparatus.

If it is desired to retain a manual tracking or viewing port in the Doppler assembly, a construction such as shown in FIG. 3B may be employed. In this construction the mirrors 41, 42 may be larger, and a pair of pinhole diaphragms 44 define the Doppler beam separation angle. An optical relay assembly consisting of objective optics 46 and relay mirrors 46a, 46b in each channel relay the collected light to the respective fiber bundles 47, and an annular green filter (a Kodak Wratten filter #57A, not shown) placed in the optical path together with an eye objective 50 provides an additional or alternative way to view the targeted vessel during Doppler measurement.

In any case, the Doppler illumination beam from laser 35 is focused to a spot of a diameter approximately equal to the diameter of the targeted vessel on the retina, and the incident beam power is attenuated to approximately five microwatts, resulting in a biologically safe level of retinal irradiance. While the photomultiplier tubes necessary to detect return irradiation at these low levels would be driven to saturation by normally encountered stray reflectances, in the illustrated apparatus the photomultiplier tubes develop an acceptable signal due in large part to the above described separation of the tracking and illumination signals in the steering system.

Figure 2:
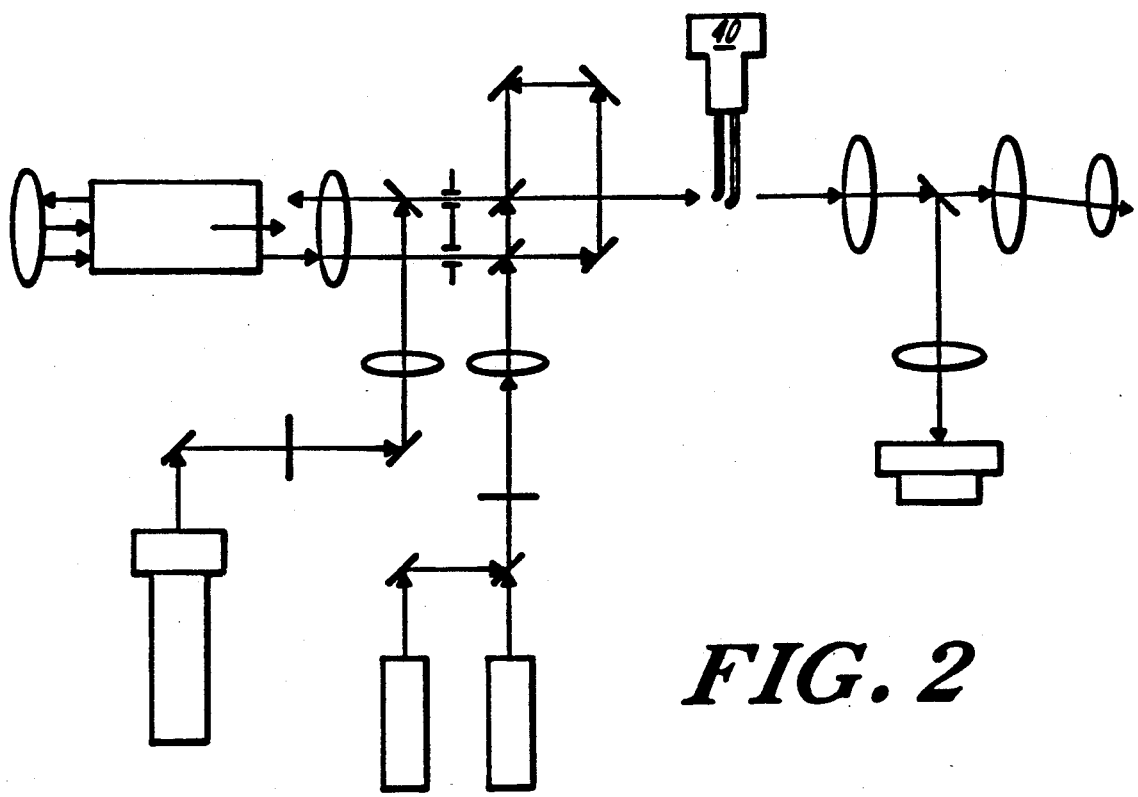
FIG. 2 illustrates another embodiment of the invention.

In a further embodiment shown in FIG. 2, the Doppler pick off and receiving assembly 40 is positioned on the opposite side of the steering system from the eye. In this embodiment, the angular relation between each pick-up and the input illumination beam is a constant, thus eliminating second order effects. A further construction difference resides in the replacement of the mirrors 41 or 42 (FIG. 1) and 46a, 46b, (FIG. 3B) with a longer fiber bundle 47 for each channel that extends directly into the return image path and conducts light to the photomultiplier tube. The bundles have a diameter of slightly over three millimeters, and translate the light from the retinal conjugate image plane without dispersion while preserving relative phase relationships.

FIG. 3A illustrates an alternative construction of the steering system 20 for use in the Doppler apparatus of FIGS. 1 or 2. In this embodiment, the x- and y- steering mirrors 21, 22 are identical to those of FIGS. 1 and 2, but the relay path between the outer faces of those mirrors consisting of mirrors 23a, 23b, 23c and associated relay lenses has been replaced by a pair of focusing mirrors 24a, 24b in a unity -magnification telecentric arrangement. This simplifies the layout and alignment of the steering assembly, reduces the number of reflective interfaces, and eliminates solid scattering media from the illumination path.

Figure 4:
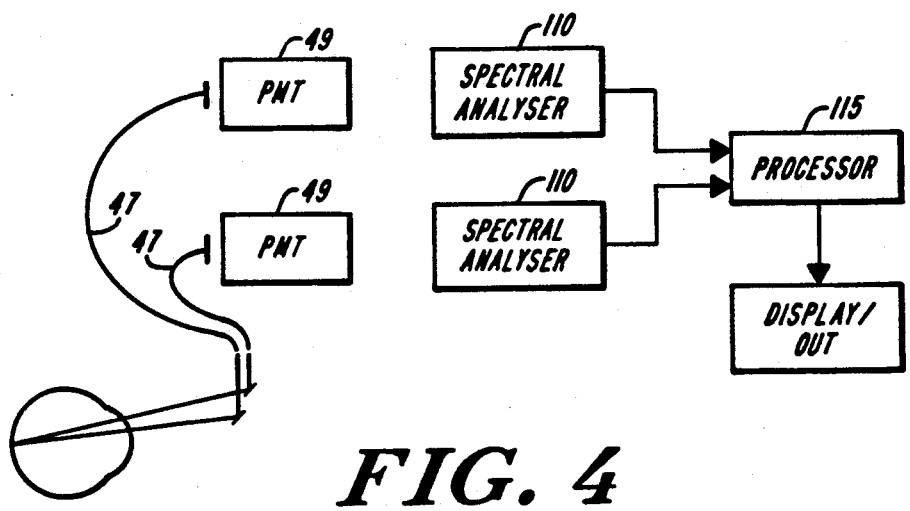
FIG. 4 illustrates the processing of Doppler signals.
Figure 5:
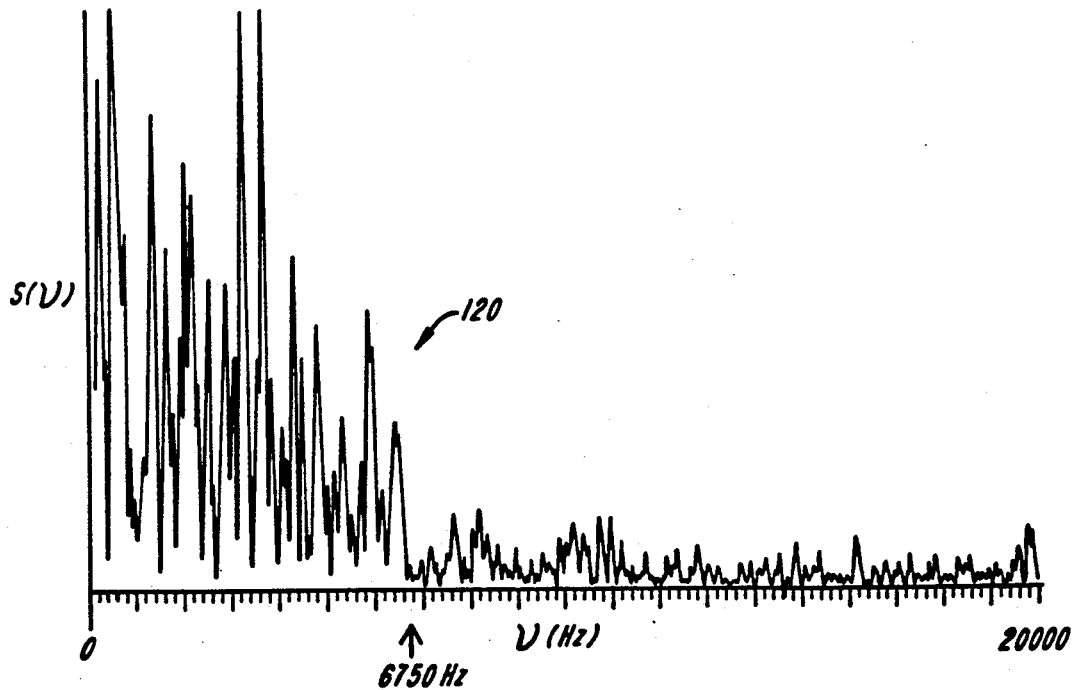
FIG. 5 illustrates a representative Doppler spectrum.

FIG. 4 illustrates the processing of collected light of the Doppler analyser. The reflected light includes light scattered from the surface of the blood vessel which serves as a reference frequency, as well as light which has Penetrated the vessel and is scattered from blood cells flowing within the vessel. These two types of light are combined on the photomultiplier tube 49 (FIG. 3), where they heterodyne to produce an electrical signal having beat frequency components corresponding to the individual velocities of the scattering cells. The electrical signal developed by each photomultiplier channel is fed to a spectral analysis system 110, which for each five millisecond interval provides an output in real time representative of the frequency components of the analysed signal, of which a representative trace is illustrated in FIG. 5. The trace is quite noisy, as it is derived from the individual motions of scattering objects which follow some general cross-sectional flow profiles within the vessel, but which also have components of motion due to thermal motion and fluid flow turbulance and irregularities. However, despite the extreme noisiness of the signal, the frequency trace does have an ascertainable upper or cut-off frequency 120 (FIG. 5) corresponding to the maximum or centerline flow velocity value of the target vessel.

In order to detect this maximum flow velocity value, the signal trace (FIG. 5) of the spectral analysis processor 110 for each diameter is digitized and passed to a processor 115 which determines the maximum frequency and displays the corresponding flow velocity. In the preferred embodiment, the cut-off frequency is identified by an integrator/differencer which constructs a new function from the output of the spectral analysis system 110 such that the new function has a maximum value at the cut-off. This processing is implemented in a software module, which for each frequency value u defines a "window" of width 2A about the value, and slides the window along the frequency scale. For each u, it subtracts the value of the frequency signal integrated over a fixed interval of width A to the right of $v$, from the value of the frequency signal integrated to the left of $v$.

The resulting function, which for each frequency $v_o$, is defined by $$f(v_o) = \sum_{v_o-A}^{v_o} s(v) - \sum_{v_o}^{v_o+A} s(v)$$

Figure 6:
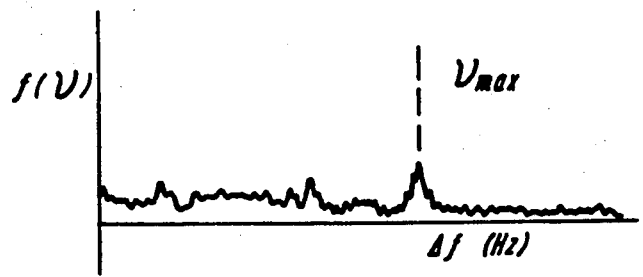
FIG. 6 illustrates the Doppler spectrum processed to identify flow rate.

(where $s(v)$ is the spectrum analyser output signal)

has a maximum precisely at the frequency where there is an extreme discontinuity in fluctuation of the signal value. FIG. 6 shows the function f(u) so defined, with the same frequency scale as illustrated in FIG. 5. Thus, it is seen that despite the jumpiness of the spectral output, the frequency corresponding to peak blood flow is readily detected.

Figure 7A:
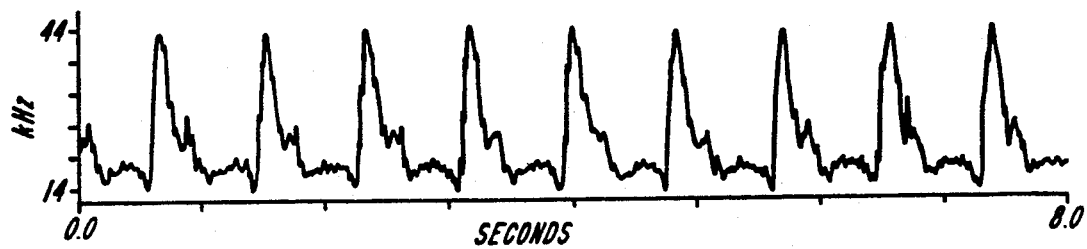
FIGS. 7, 7(a), (b), and (c) illustrate the instantaneous maxima of Fourier spectra plotted over time, and the Doppler signal processing.
Figure 7B:
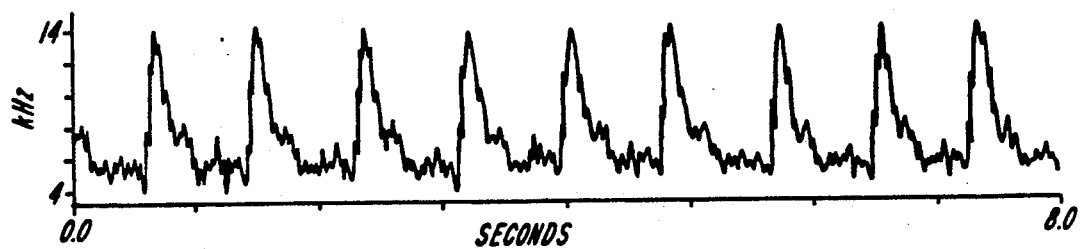
Figure 7C:
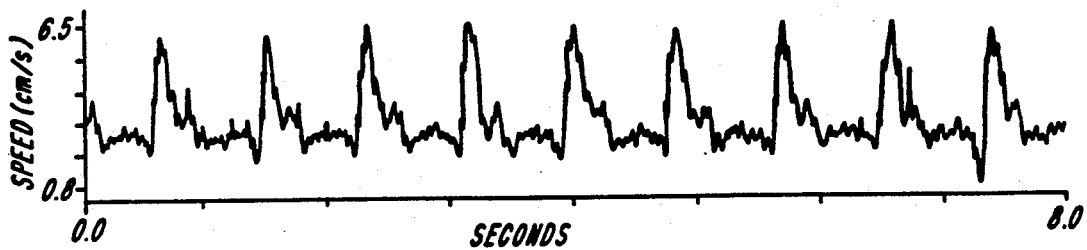

FIGS. 7, 7A, 7B and 7C illustrate the basic signal processing of the above-described system. The line A of FIG. 7A shows an eight second signal trace consisting of the frequency maximum at each instant in time derived by the spectral analysis system 110 from the output of one photomultiplier tube 49 when the Doppler illumination spot is aimed at a retinal artery. The line of FIG. 7B shows the corresponding trace of the other photomultiplier. Each channel has different absolute frequency range, owing to their different light collection angles, but both show the distinctive periodic pulses associated with arterial flow due to the cardiac pumping cycles. The line of FIG. 7C shows the blood flow velocity equal to a constant, for a given eye and instrument configuration, times the difference between lines A and B. Specifically, line C represents the peak instantaneous centerline blood flow velocity, which, at a given instant, is directly proportional to the difference in peak or cutoff frequencies of the two signals, lines A and B.

Figure 7:
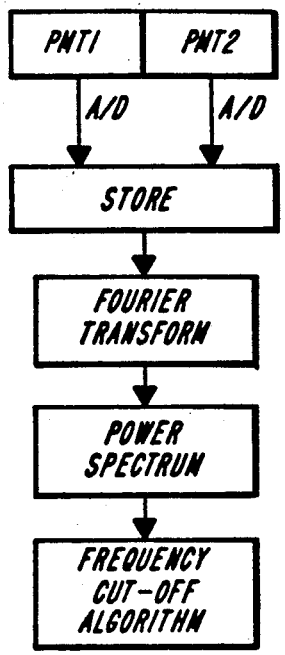

FIG. 7 illustrates the overall operation of the spectral analysis system and processor of FIG. 4. Each PMT analog output is A/D converted and stored in a computer-accessible form, e.g., on a disc. A software Fourier transform module analyses each t-second block of signal values and computes its power spectrum. Each power spectrum (channels 1 and 2) is Processed by the frequency cut-off detection algorithrum described above in relation to FIG. 6. In the prototype instrument, the processor operated in real time to digitize and process eighty-nine five-millisecond samples per second for each channel, producing the highly detailed traces illustrated in the figures.

It further bears note that in FIGS. 4 and 7, the function of the spectral analysis system and the processor are not clearly separated, for the reason that in the preferred embodiment the spectral analysis and subsequent signal processing steps may be primarily performed by the processor, which may be a microcomputer equipped with numerical analysis software and with Fourier transform software.

In a preferred embodiment of the invention, further functions are performed in the processor on other optoelectronic signals to develop a number of specific indicators or pieces of clinical information as more fully described below, including volumetric blood flow outputs, vessel blockage or flow anomaly determinations, and normative comparison of circulation.

It should be noted that because the Doppler analysis module uses the light reflected from the outside of a blood vessel as a reference beam, frequency shift effects caused by motion of the eye or of the illumination spot cancel out, and the detected flow rate is substantially the same whether the focused Doppler beam is stationary or is moving along the long direction of the blood vessel, with or opposed to the flow direction. For this reason, the tracking system need not control motion in two dimensions, but may be a one-dimensional tracker with its tracking components configured in an orientation to correct only for motion of the eye in a direction transverse to the vessel at which the Doppler beam 100 is directed. This may be accomplished, for example, when using a tracker as shown in the aforesaid U.S. patent, by choosing a tracking target vessel which either is, or lies parallel to, the vessel on which Doppler measurements are to be taken, and by tracking motion transverse to that tracking target to develop steering correction signals.

It is also possible to use a two-axis tracking system to stabilize the Doppler beam and return light for analysis and imaging.

In one presently preferred embodiment of the invention, a single-axis tracker is employed, and output signals from the tracking CCD provide quantitative measurements to convert the Doppler output to absolute volumetric flow measurements.

Figure 8:
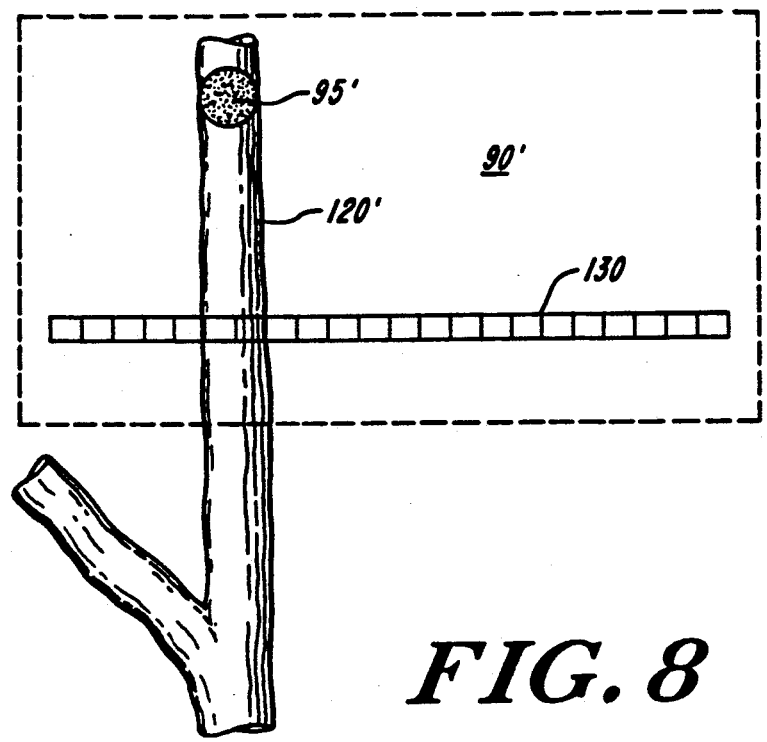
FIG. 8 illustrates tracking and Doppler illumination of a retinal vessel.

FIG. 8 illustrates details of the Doppler imaging of such a device. A retinal vessel 120 which may have a diameter of under fifty to a few hundred micrometers, is illuminated by a green tracking beam 90 which has a round or rectangular cross section of approximately 0.5-1.0 mm diameter, and the Doppler illumination beam is focused to a spot 95 on the same vessel. The retinal region illuminated by the tracking beam 90 is imaged and aligned, via the steering system 20 as described above, as an image 90' onto a CCD line array 130 which is oriented perpendicularly to the image 120' of the vessel. A magnifying objective assembly of five to twenty five magnifications is used, such that the CCD lies entirely within the image 90' of the tracking beam. For example, for a linear array consisting of a one by two hundred fifty-six pixel CCD of approximately twelve millimeters length, a twenty-five power objective assures that the image of a five hundred micrometer wide tracking beam will cover the CCD 130. Correspondingly, the image of a fifty to one hundred micrometer retinal blood vessel will cover approximately twenty-five to fifty pixel elements of the CCD.

Figure 9:
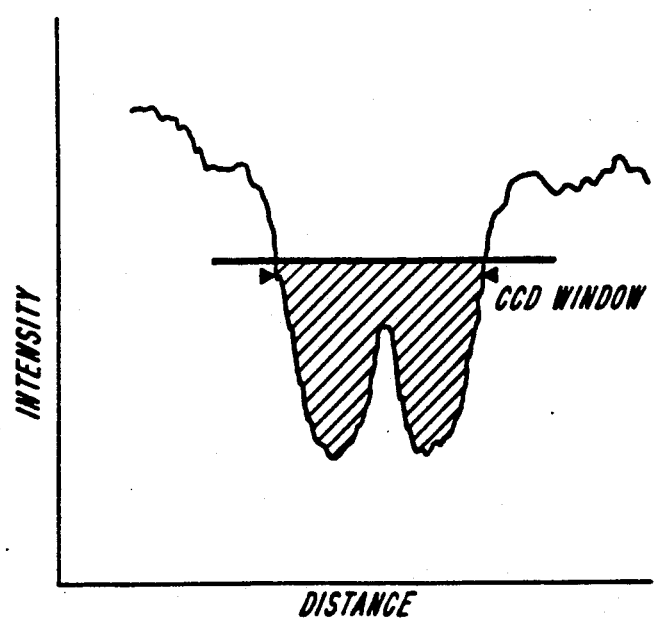
FIG. 9 illustrates the CCD image signal for determining vessel diameter.

FIG. 9 illustrates the sensed illumination values, along the length of the CCD, of tracking light reflected from the retina. The characteristic double-valley minimum in detected light intensity corresponds to the blood vessel image, with a central local maximum corresponding to the specular reflection from the top center of the vessel wall. The full width half maximum points of the illumination values, illustrated by the two arrows, correspond to the vessel diameter d.

In the above described preferred embodiment, the tracker not only polls the CCD at one millisecond intervals to determine position-correcting control signals from the steering mirrors, but processes the CCD output to determine the vessel diameter d by solving for the full width half maximum points.

In a further preferred embodiment, the processor further performs internal computations to combine the detected flow velocity and vessel diameter, and to compute an absolute volumetric flow rate.

The preferred processing for determining the volumetric flow rate proceeds as follows. First, the processor integrates the centerline flow velocity (FIG. 5) over a time interval, by numerical processing, and divides the integral to determine an average centerline blood speed "acb". Next, the processor determines the vessel cross-sectional area $A = \pi(d/2)^2$ from the vessel diameter d. For sufficiently large vessels, (over about fifty micrometers) the assumption of Poiseuille flow holds, and the total volumetric flow is calculated to be $A(acb)/2$.

This capability of directly computing the volume of blood flow in a vessel during observation is advantageously augmented in several further embodiments of the invention to provide systemic measurements of total flow, branch flow anomalies, blockage or general sufficiency. In one such embodiment, the processor stores a memory table listing the range of normal blood flow as a function of vessel size. This information may be stored separately for arteries (recognizable by their distinctly pulsatile flow) and for veins (having a more uniform flow rate).

Once a vessel has been targeted by the tracker and its diameter d determined, the stored normal value indexed by the diameter d is retrieved and the normal value is compared to the computed flow value to determine whether there is an anomaly.

In another embodiment, the "normal" value need not be a predetermined universal value, but may be determined by measuring and storing the flow values for vessels of varying diameters in a patient's healthy eye; and the comparison is then made against the measured flow velocity or volume values of the other eye. It will be understood that the "normal" values need not be functions only of diameter, but may also be ordered or indexed as functions of the subject's sex or age, the subject's blood pressure, or other clinical parameter.

Figure 10:
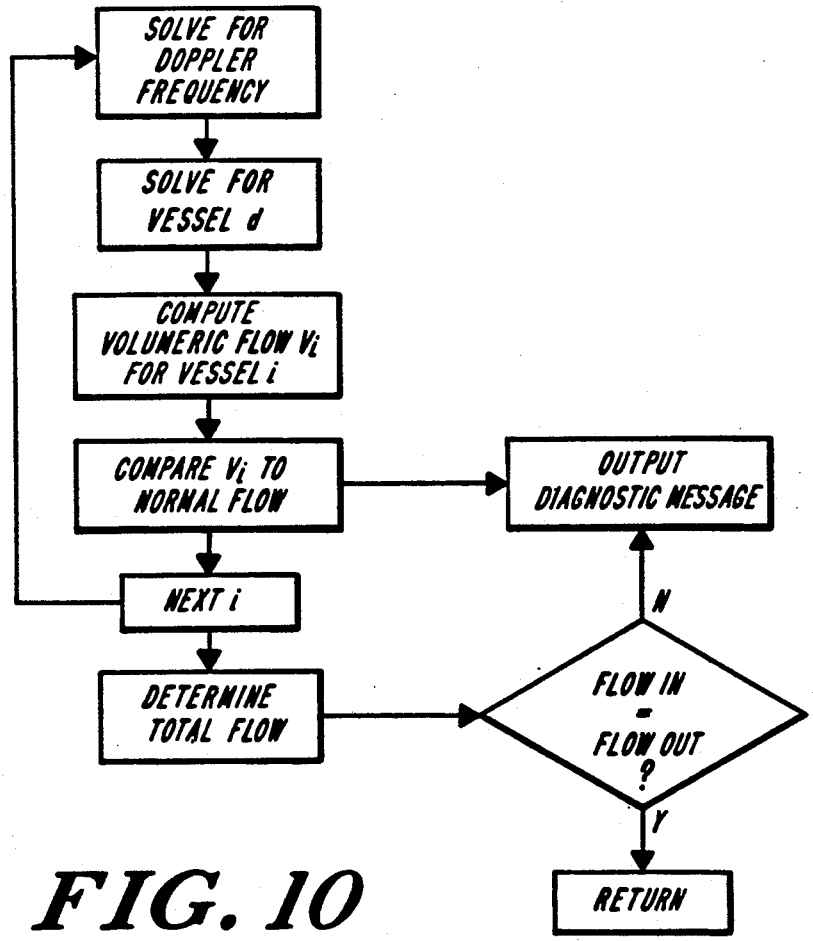
FIG. 10 illustrates processing of a diagnostic Doppler measurement system.

In a further variation of this embodiment, the processor may include means for summing the flow rates of each of a plurality of arteries, and for summing or subtracting the flow of a plurality of veins, thus providing indications of the blood flow for whole regions of the retina. An imbalance in the total flows into or out of a retinal region provides an indication of flow anomaly indicative of possible pathology. In other embodiments, a simple comparison to a threshhold flow value may indicate a particular pathology such as hemorrhaging, or a detached retina. General processing states for one or more of these further systems are illustrated in FIG. 10.

This completes a description of the invention and several representative embodiments thereof, together with subsidiary details and variations of construction. The invention being thus disclosed, modification and equivalents thereof will occur to those skilled in the art, and such modifications and equivalents are considered to lie within the scope of the invention, as determined by the claims appended hereto.

What is claimed is:

1. Apparatus for the measurement of retinal blood flow in an eye of a subject, such apparatus comprising a first light source for forming and projecting along a first path an illumination beam which converges to an illumination spot on a retinal vessel, a second light source for forming and projecting along a tracking Path at least one beam of tracking light distinct from light of the first light source, light collection means for separately collecting light from the illumination spot reflected along two directions separated by a fixed angle, Doppler analysis means for analyzing light collected by the light collection means to provide an indication of blood flow in the retinal vessel illuminated by the illumination spot, an optical beam steering system for controllably directing a beam of light incident thereon to the retina, said optical beam steering system moving in response to control signals, and being located and aligned to receive and direct to the retina said illumination beam and simultaneously to receive light from said beam of tracking illumination reflected from the retina, imaging means for forming, back through said optical beam steering system, an image of retinal tissue illuminated by said tracking light, and tracking means responsive to motion of the image of retinal tissue for providing a control signal to said steering system that maintains the image stationary, said tracking means being operated at a rate effective to limit jitter such that the illumination spot remains on the retinal vessel and the Doppler analysis means detects the flow of blood in said vessel.

2. Apparatus according to claim 1, wherein said beam-steering system comprises separated forward and reverse paths defined by different faces of a common set of steering mirrors, said illumination beam and said beam of tracking light being steered along said forward path to the eye, and said image being formed along said reverse path from the eye.

3. Apparatus according to claim 2, wherein said light collection means collects light which returns along said reverse path from the eye past a said steering mirror.

4. Apparatus according to claim 2, wherein said common set of steering mirrors comprises a pair of galvanometer controlled steering mirrors, each mirror being metallized on both sides.

5. Apparatus according to claim 1, wherein said illumination beam converges to a spot of approximately fifty micrometers diameter.

6. Apparatus according to claim 1, wherein said collection and said imaging means each collect light passing through a different region of the eye pupil.

7. Apparatus according to claim 1, wherein said Doppler analysis means includes a spectral analysis system which operates in real time to determine a frequency distribution indicative of blood flow velocity.

8. Apparatus according to claim 7, wherein said Doppler analysis means further includes means for determining a volumetric blood flow rate.

9. Apparatus according to claim 7, further including a means for comparing a blood flow rate with a reference blood flow rate.

10. Apparatus according to claim 9, wherein said reference flow rate is a stored flow rate indexed by at least one of vessel diameter and age of subject.

11. Apparatus according to claim 1, wherein said light collection means includes a fiber for translating received light without dispersion while preserving phase relationships.

12. Apparatus according to claim 1, further comprising means for determining the diameter of the retinal vessel.

13. Apparatus according to claim 12, wherein the tracking means detects motion of the retinal image on a photodetector array and the means for determining diameter determines the size of the image of a retinal vessel on the array.

14. Apparatus according to claim 12, further comprising processing means for determining at least one of a leakage condition, a blockage condition, and total blood flow.

15. Apparatus according to claim 1, further comprising means for processing the indication of blood flow to identify vascular pathology.

16. Apparatus for he Doppler measurement of retinal blood flow, comprising
operator viewing means for aiming the apparatus at a retina
first means for directing coherent light at a retinal vessel
second means for collecting light scattered by blood flowing in the retinal vessel and directing it at a photodetector to develop an electrical signal
A/D conversion means for converting the electrical signal to a digital signal
tracking means operative on a vessel image for stabilizing aim of the apparatus at the retinal vessel as coherent light is directed at and scattered light is collected from the vessel, and
digital processing means operative on the digitized signal to perform a fast Fourier transform and develop a measure of blood speed in the retinal vessel, said processing means further communicating with said tracking means to develop an indication of vessel diameter and to functionally combine said measure of blood speed and indication of diameter, operating in real time to determine a retinal circulation value as the apparatus is aimed at the retina, thereby achieving real time in vivo clinical evaluation of observed tissue.

17. Apparatus according to claim 16, wherein said processing means determines a volumetric flow rate of blood in the retinal vessel.

18. Apparatus according to claim 16, further comprising data storage means for containing a compilation of normal values of retinal circulation, and wherein the processing means compares a determined value to a stored normal value to produce a diagnostic output.

19. A method for the measurement of retinal blood flow in an eye of a subject, such method comprising the steps of
projecting along a first path an illumination beam which converges to an illumination spot on a retinal vessel,
projecting along a tracking path at least one beam of tracking light distinct from light of the illumination beam,
separately collecting light reflected from the illumination spot along two directions separated by a fixed angle,
Doppler analyzing the collected light to provide an indication of blood flow in the retinal vessel illuminated by the illumination spot,
providing an optical beam steering system for controllably directing a beam of light incident thereon to the retina, said optical beam steering system moving in response to control signals, and locating and aligning said optical beam steering system to receive and direct to the retina said illumination beam and simultaneously to receive light from said beam of tracking illumination reflected from the retina,
forming, back through said optical beam steering system, an image of retinal tissue illuminated by said tracking light, and
tracking motion of the image of retinal tissue and providing a control signal to said steering system that maintains the image stationary, said tracking being performed at a rate effective to limit jitter such that the illumination spot remains on the retinal vessel and the step of Doppler analyzing determines the rate of flow of blood in said vessel.

20. The method of claim 19, wherein said optical beam steering system comprises separated forward and reverse paths defined by different faces of a common set of steering mirrors, and wherein said illumination beam and said beam of tracking light are steered along said forward path to the eye, while said image is formed along said reverse path from the eye.

21. The method of claim 20, wherein the step of collecting light collects light which has returned along said reverse path from the eye past a said steering mirror.

22. A method for the Doppler measurement of retinal blood flow, such method comprising the steps of viewing the retina through an apparatus and
directing coherent light at a retinal vessel
collecting light scattered from blood flowing in the retinal vessel and directing it at a photodetector to develop an electrical signal
digitizing the electrical signal
detecting motion of an image of a vessel to develop control signs for stabilizing aim of the instrument on the vessel as coherent light is directed at and scattered light is collected from the vessel, and
digitally processing the digitized electrical signal in real time with a fast Fourier transform to develop a measure of blood speed in the retinal vessel while determining the vessel diameter from said image of the vessel, and functionally combining the blood speed and vessel diameter in real time to provide a diagnostic indicator of retinal circulation as the apparatus is aimed at the retina thereby achieving real time in vivo clinical evaluation of actual blood flowing in observed tissue.

23. The method of claim 22, wherein the step of processing includes computing a volumetric flow rate of blood in the vessel.

24. The method of claim 22, wherein the diagnostic indicator output is derived by comparison of measured blood flow information to stored blood flow information.

25. The method of claim 22, further comprising the steps of
functionally combining information as the apparatus is aimed at plural retinal vessels, and
comparing the functionally combined information to a stored table of normative measurements to produce said diagnostic indicator.

26. The method of claim 22, further comprising the step of functionally combining blood flow information from plural distinct arterial and venous vessels to produce a diagnostic indicator of circulatory leakage or blockage.

27. Apparatus according to claim 16, wherein the processing means further includes program sequence means for combining a plurality of successive values of retinal circulation as the apparatus is aimed at different retinal vessels, and means for detecting circulatory leakage or blockage conditions.

* * * * *

UNITED STATES PATENT AND TRADEMARK OFFICE
CERTIFICATE OF CORRECTION

PATENT NO. : 5,106,184
DATED : April 21, 1992
INVENTOR(S) : Michael T. Milbocker, et. al.

It is certified that error appears in the above-indentified patent and that said Letters Patent is hereby corrected as shown below:

On the Title page, item [75], inventor: delete "Inventor" and insert -- Inventors --, and after "Michael T. Milbocker, Somerville, Mass." insert -- Gilbert T. Feke, Stoneham, Mass. --

Signed and Sealed this

Twenty-seventh Day of July, 1993

Attest:

MICHAEL K. KIRK

*Attesting Officer*          *Acting Commissioner of Patents and Trademarks*